United States Patent [19]

Hamann et al.

[11] Patent Number: 5,681,972
[45] Date of Patent: Oct. 28, 1997

[54] PROCESS FOR PREPARING HIGHLY CONCENTRATED, FREE-FLOWING AQUEOUS SOLUTIONS OF BETAINES

[75] Inventors: Ingo Hamann, Bad Orb; Hans-Jürgen Köhle, Schluchtern; Winfried Wehner, Neuhof, all of Germany

[73] Assignee: Witco Surfactants GmbH, Germany

[21] Appl. No.: 413,190

[22] Filed: Mar. 30, 1995

[30] Foreign Application Priority Data

Apr. 12, 1994 [DE] Germany .................. 44 12 481.3

[51] Int. Cl.$^6$ .................................................. C07C 231/00
[52] U.S. Cl. .................. 554/69; 554/52; 554/68; 252/546
[58] Field of Search ................ 252/546; 554/52, 554/68, 69

[56] References Cited

U.S. PATENT DOCUMENTS 3,225,074  12/1965  Cowen et al. ............... 260/404.5
4,832,871  5/1989  Bade ............................ 252/546
4,861,517  8/1989  Bade ............................ 252/546
5,204,375  4/1993  Kusakawa et al. .......... 514/784

FOREIGN PATENT DOCUMENTS 0 353 580  2/1990  European Pat. Off. .
3 613 944  8/1987  Germany .
3 726 322  12/1988  Germany .

*Primary Examiner*—Gary Geist
*Assistant Examiner*—Deborah D. Carr
*Attorney, Agent, or Firm*—Scully, Scott, Murphy & Presser

[57] ABSTRACT

The invention relates to a process for preparing highly concentrated, free-flowing and pumpable, aqueous solutions of betaines by quaternization of compounds containing tertiary amine nitrogen with omega-halocarboxylic acids by known processes, which is characterized in that a) 30–100 equivalent-%, based on the amount of omega-halocarboxylic acid used, of $Mg(OH)_2$ and/or $Ca(OH)_2$ and b) 0–70 equivalent-%, based on the amount of omega-halocarboxylic acid used, of one or more NaOH, KOH and $NH_4OH$ are added to the reaction mixture before or during the quaternization reaction.

17 Claims, No Drawings

PROCESS FOR PREPARING HIGHLY CONCENTRATED, FREE-FLOWING AQUEOUS SOLUTIONS OF BETAINES

BACKGROUND OF THE INVENTION

The present invention relates to a process for preparing highly concentrated, free-flowing aqueous solutions of betaines, which have solids contents of up to 50% by weight.

In recent years, betaines have become established in the cosmetic industry as a significant constituent of formulations, in particular for hair and body cleansing. They have the ability to form a dense and creamy foam which remains stable over a long period of time even in the presence of other surfactants, soaps and additives, together with recognized good cleansing properties without any irritating side effects, even for sensitive skin.

The preparation of betaines is comprehensively described in the relevant patent and specialist literature (e.g., U.S. Pat. No. 3,225,074). In general, compounds containing tertiary amine nitrogen atoms are here reacted with omega-halocarboxylic acids or salts thereof in aqueous or water-containing media. The compounds containing tertiary amine nitrogen atoms used are, in particular, one or more fatty acid amides of the general formula (I)

$$R^3\text{—CONH—}(CH_2)_m\text{—}NR^4R^5 \qquad (I)$$

where $R^3$ is the alkyl radical, or alkylene radical with 1–3 carbon-carbon double bonds, of a fatty acid, which can if desired, be branched, if desired contain multiple bonds and, if desired, contain 1–6 hydroxyl groups, and $R^4$ and $R^5$ are identical or different alkyl radicals having 1–4 carbon atoms and m can be 1–3.

The alkyl or alkylene radical $R^3$ can here be derived from the natural or synthetic fatty acids having 6–20 carbon atoms, preferably from the natural plant or animal fatty acids having 8–18 carbon atoms, and also their naturally occurring specially set mixtures with one another or among one another.

Suitable fatty acids are, for example, caproic acid, caprylic acid, capric acid, lauric acid, palmitic acid, stearic acid, linoleic acid, linolenic acid and ricinoleic acid.

Preference is given to the naturally occurring fatty acid mixtures having a chain length of 8–18 carbon atoms, such as coconut oil acids or palm kernel oil acids, which can, if desired, be hardened by suitable hydrogenation methods.

These fatty acids or fatty acid mixtures are converted into the fatty acid amides having tertiary nitrogen atoms, of the general formula (I), by means of the conventional condensation reaction at 140°–200° C. with one or more amines of the general formula (II)

$$H_2N\text{—}(CH_2)_m\text{—}NR^4R^5 \qquad (II)$$

in which $R^4$ and $R^5$ and m are as defined for the formula (I).

The subsequent quaternization reaction to give betaines of formula (III)

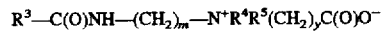

$$R^3\text{—C(O)NH—}(CH_2)_m\text{—}N^+R^4R^5(CH_2)_yC(O)O^-$$

wherein $R^3$, $R^4$, $R^5$ and m are as defined for the formulae (I) and (II) and y can be 1, 2 or 3, can be carried out according to the processes known in the literature.

In general, omega-haloalkylcarboxylic acids, preferably the sodium salt of chloroacetic acid, are here added in aqueous medium to the fatty acid amide of the formula (I) and the quaternization is carried out in a reaction taking a number of hours at about 80°–100° C. Depending on the fatty acid or fatty acid mixture used, a minimum amount of water has to be present to maintain stirrability as the reaction proceeds. The commercial betaine concentration of the solutions prepared in this way is therefore about 30% by weight or below.

However, to save storage and transport costs and also for formulation reasons in further processing, a higher concentration is greatly desired in many cases.

In the past, therefore, proposals were made for a number of processes which were supposed to solve this problem. Thus, DE-C 3 613 944 discloses a process in which the quaternization is carried out in a polar organic solvent having a water content of 20% by weight, and the solvent is then completely or partially removed by distillation, and the concentration is then adjusted to that desired using a solvent which is usable in the application.

Apart from the process being technically complicated and expensive, organic solvents are often undesired in further processing in cosmetic formulations.

Although the process described in DE-C 3 726 322 can be carried out without organic solvents, the amount of water required for the quaternization reaction has to be removed again from the reaction product by distillation, with the pH of the solution having to be adjusted by relatively high amounts of acid, before or after adjustment to the desired concentration, to values of 1–4.5 which are atypical of skin.

According to EP-A 0 353 580, non-ionogenic, water-soluble surfactants are added to the reaction mixture of fatty acid amide and haloalkylcarboxylic acid before or during the quaternization reaction or to the solution of the betaine obtained, in such amounts that the finished solution contains 3–20% by weight of water-soluble surfactants.

The non-ionogenic surfactants used are polyoxyethylene ethers which have to contain 10–250 oxyethylene units for sufficient water solubility.

However, polyoxyethylene ethers having relatively high proportions of oxyethylene units have proven not to be unproblematical in respect of their biodegradability.

There has therefore been a continuing need for highly concentrated, free-flowing and pumpable, aqueous solutions of betaines, which are free of lower alcohols such as methanol, ethanol, propanol or isopropanol.

BRIEF SUMMARY OF THE INVENTION

It has now surprisingly been found that free-flowing and pumpable solutions of betaines having a concentration of up to about 45% by weight, based on dry substance, can be prepared from the reaction mixture of fatty acid amide and omega-haloalkylcarboxylic acid by known processes if alkaline earth metal hydroxides such as, in particular, $Mg(OH)_2$ and/or $Ca(OH)_2$ are added during the quaternization reaction.

The invention accordingly provides a process for preparing highly concentrated, free-flowing and pumpable, aqueous solutions of betaines by quaternizing one or more compounds containing tertiary amine nitrogen with one or more omega-halocarboxylic acids which is characterized in that the quaternization is carried out in the presence of a) 30–100 equivalent-%, based on the amount of omega-halocarboxylic acid reacted, of $Mg(OH)_2$ and/or $Ca(OH)_2$ and b) 0–70 equivalent-%, based on the amount of omega-halocarboxylic acid reacted, of one or more of NaOH, KOH and $NH_4OH$, which hydroxide compound or compounds are added to the reaction mixture before or during the quaternization reaction.

The invention further provides for the modification of this process, which is characterized in that the component a)

used is 30–100 equivalent-%, based on the amount of omega-halocarboxylic acid used, of LION.

DETAILED DESCRIPTION OF THE INVENTION

In carrying out the process of the invention, the initially charged omega-halocarboxylic acid is neutralized with a mixture of sodium hydroxide and magnesium and/or calcium hydroxide, and the quaternization reaction of the one or more compounds of formula (I) is carried out by reaction for a number of hours in an aqueous medium at 80°–100° C.

A further process variant for preparing highly concentrated, free-flowing and pumpable, aqueous solutions of betaines comprises carrying out the reaction by any of the known processes using haloacetic acid such as chloroacetic acid and NaOH or using the sodium salt of e.g. chloroacetic acid, with the modification that lithium, magnesium or calcium salts, alone or in admixture, are added as viscosity regulators before or during the quaternization reaction.

The invention accordingly further provides a process for preparing highly concentrated, free-flowing and pumpable, aqueous solutions of betaines by quaternization of compounds containing tertiary amine nitrogen with omega-halocarboxylic acids according to known processes, which is characterized in that 0.5–5% by weight, based on the total mixture, of at least one of the salt compounds

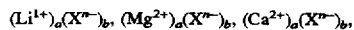

$(Li^{1+})_a(X^{n-})_b, (Mg^{2+})_a(X^{n-})_b, (Ca^{2+})_a(X^{n-})_b,$ where $X^{n-}$ is the radical of an organic or inorganic acid, and n is 1–3, and a and b are integers, wherein a, b and n are selected such that the salt compounds are neutral in charge, is added to the mixture of fatty acid amide of the general formula (I) and the Na, K or $NH_4$ salt of the omega-halocarboxylic acid before or during the quaternization reaction.

$X^{n-}$ is the anion of a monobasic or polybasic organic acid, in particular monobasic to tribasic acids, insofar as they form water-soluble salts with Li, Mg and/or Ca, such as $C_1$–$C_5$-monocarboxylic acids, preferably acetic acid.

According to the invention, however, preference is given to using LiCl, $MgCl_2$ and/or $CaCl_2$ in the form of the anhydrous salts or the hydrates.

The total amount of the one or more compounds $(Li^{+1})_a$ $(X^{n-})_b, (Mg^{2+})_a(X^{n-})_b$ and $(Ca^{2+})_a(X^{n-})_b$ is between 0.5–5% by weight, based on the total mixture.

A further process variant comprises completely or partially replacing all or some of the $Li^+$, $Mg^{2+}$ and/or $Ca^{2+}$ salts by one or more compounds of the general formula (IV)

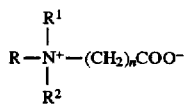

$$R-\underset{\underset{R^2}{|}}{\overset{\overset{R^1}{|}}{N^+}}-(CH_2)_nCOO^- \qquad (IV)$$

wherein R, $R^1$ and $R^2$ are independently identical or different straight or branched alkyl radicals having 1–10 carbon atoms optionally substituted with 1–6 hydroxyl groups, in particular methyl radicals, and n is 1–3 and n is preferably 1, with mixtures of 0.5–2% by weight of one or more of the aforementioned salt compounds of Li, Mg and/or Ca, and 0.5–5% by weight of betaine being preferred according to the invention.

Compounds of the general formula (IV) which can also be used according to the invention are quaternization products of dimethylethanolamine, methyldiethanolamine or alkyl ($C_2$–$C_{10}$)-dimethytamine and monochloroacetic acid, but in particular the trimethylglycine or "betaine" occurring naturally in sugar beet (*Beta vulgaris*).

These compounds can be added to the reaction mixture as mixtures together with the salts, simultaneously with salt addition or after salt addition, in amounts of 1–5% by weight, based on the aqueous solution, with a total content of (salt+betaine) being above 5 to 7% by weight, based on the aqueous solution, generally bringing no advantages.

According to the invention, preference is given to mixtures of 0.5–2% by weight of one or more of the aforementioned compounds of Li, Mg and/or Ca, and 0.5–5% by weight of betaine.

The carrying out of the process follows the processes known in the prior art, with the significant change comprising the addition of the one or more alkaline earth metal salts and/or the LiCl before or during the quaternization reaction.

The preferred procedure according to the invention is to neutralize the initially charged omega-halocarboxylic acid with sodium hydroxide and to add 0.5–5.0% by weight, based on the total mixture, of one or more of LiCl, $MgCl_2$ and/or $CaCl_2$ before or during the reaction, which takes a number of hours, in an aqueous medium at 80°–100° C.

Analytical methods

Dry content:

The dry content is determined by drying the material at 105° C. to constant weight. These values are determined by the standard methods of the German Association for Fat Chemistry (DGF): B-II.

Acid number (AN):

The acid number is a measure of the free acids contained in fats and technical grade fatty acids. It indicates the number of milligrams of potassium hydroxide which is required to neutralize 1 gram of substance or technical grade fatty acids (mg KOH/g). These values are determined by the standard methods of the German Association for Fat Chemistry (DGR): D-IV 2a.

Ester number (EN):

The ester number is a measure of the esters contained in fats and technical grade fatty acids. It indicates the number of milligrams of potassium hydroxide which is required to saponify 1 gram of substance or technical grade fatty acids (mg KOH/g). These values are determined by the standard methods of the German Association for Fat Chemistry (DGF): C-V 4.

Total amine number (TAN), tertiary amine number (TerAN):

The total amine number indicates the number of milligrams of potassium hydroxide which are equivalent to the total basicity of 1 gram of the amine compound (mg KOH/g).

The tertiary amine number indicates the number of milligrams of potassium hydroxide which are equivalent to the tertiary amine basicity of 1 gram of the amine compound (mg KOH/g).

The values are determined by the American Oil Chemists Society (A.O.C.S.) Official Method Tf 2a-64.

Chloride:

The chloride content is determined potentiometrically against a standard silver nitrate solution. The electrode used is a combination silver chloride electrode. The values are determined by the standard methods of the German Association for Fat Chemistry (DGF): H-III 9.

EXAMPLES

Example 1

Preparation of the aminamide:

In a reactor fitted with stirrer, thermometer and distillation attachment, 98.0 kg of hardened coconut oil were admixed under an inert gas atmosphere with 56.8 kg of dimethylaminopropylamine and heated to 150°–160° C. and boiled under reflux. After the amidation was complete (ester number <10 mg KOH/g), the excess amine was distilled off in vacuo at this temperature. The distillation was complete, since the difference between the total amine number and tertiary amine number was less than 3 mg KOH/g. The aminamide obtained had a TAN of 170.6 mg KOH/g, a TerAN of 168.6 mg KOH/g and an ester number of 2.8 mg KOH/g.

Example 2

97.3 g of monochloroacetic acid were diluted with 504 g of water while cooling in a 1-liter flask fitted with stirrer, internal thermometer and pH electrode and carefully neutralized with 27.8 g of lithium hydroxide. After addition of 320 g of the aminamide from Example 1, the reaction mixture was stirred at 80°–90° C., the pH being kept between 8 and 8.5. For this purpose, a further total of 2.9 g of lithium hydroxide were required. After a reaction time of about 9 hours, the alkylation was complete. A betaine mixture had formed and was allowed to cool to 50° C., and the pH was adjusted to 5.4 using 5.2 g of citric acid.

The final product was a clear liquid having a viscosity of 130 mPas at 20° C., a dry residue of 45.7 and a chloride content of 3.8%.

Example 3

97.3 g of monochloroacetic acid were diluted with 515 g of water while cooling in a 1 liter flask fitted with stirrer, internal thermometer and pH electrode and carefully neutralized with 31 g of magnesium hydroxide. After addition of 320 g of the aminamide from Example 1, the reaction mixture was stirred at 80°–90° C., the Ph being kept between 8 and 8.5. For this purpose, a further total of 2.9 g of magnesium hydroxide were required. After a reaction time of about 8 hours, the alkylation was complete. A betaine mixture had formed and was allowed to cool to 50° C., and the pH was adjusted to 5.1 using 6.5 g of 50% strength citric acid solution.

The final product was a clear liquid having a viscosity of 90 mPas at 20° C., a dry residue of 45.0% and a chloride content of 3.8.

Example 4

97.3 of monochloroacetic acid were diluted with 520 g of water while cooling in a 1 liter flask fitted with stirrer, internal thermometer and pH electrode and carefully neutralized with 38.9 g of calcium hydroxide. After addition of 320 g of the amminamide from Example 1, the reaction mixture was stirred at 80°–90° C., the pH being kept between 8 and 8.5. For this purpose, a further total of 2.9 g of calcium hydroxide were required. After a reaction time of about 8 hours, the alkylation was complete. A betaine mixture had formed and was allowed to cool to 50° C. and the pH was adjusted to 5.9 using 3 g of citric acid.

The final product was a clear liquid having a viscosity of 170 mPas at 20° C., a dry residue of 45.1% and a chloride content of 3.6%.

Example 5

97.5 g of monochloroacetic acid were diluted with 500 g of water while cooling in a 1 liter flask fitted with stirrer, internal thermometer and pH electrode and carefully neutralized with 7.5 g of magnesium hydroxide and 63 g of sodium hydroxide solution (50%). After addition of 320 g of the aminamide from Example 1, the reaction mixture was stirred at 80°–90° C., the pH being kept between 8 and 8.5. For this purpose, a further total of 6.0 g of sodium hydroxide (as 50% strength solution) were required. After a reaction time of about 8 hours, the alkylation was complete. A betaine mixture had formed and was allowed to cool to 50° C. and the pH was adjusted to 5.4 using 3.5 g of citric acid.

The final product was a clear liquid having a viscosity of 128 mPas at 20° C., a dry residue of 44.6% and a chloride content of 3.6%.

Example 6

97.3 g of monochloroacetic acid were diluted with 500 g of water while cooling in a 1 liter flask fitted with stirrer, internal thermometer and pH electrode and carefully neutralized with 15 g of magnesium hydroxide and 44 g of sodium hydroxide solution (50%). After addition of 320 g of the aminamide from Example 1, the reaction mixture was stirred at 80°–90° C., the pH being kept between 8 and 8.5. For this purpose, a further total of 4.6 g of sodium hydroxide (as 50% strength solution) were required. After a reaction time of about 8 hours, the alkylation was complete. A betaine mixture had formed and was allowed to cool to 50° C. and the pH was adjusted to 5.6 using 3.5 g of citric acid.

The final product was a clear liquid having a viscosity of 210 mPas at 20° C., a dry residue of 45.9% and a chloride content of 3.7%.

Example 7

97.3 g of monochloroacetic acid were diluted with 500 g of water while cooling in a 1 liter flask fitted with stirrer, internal thermometer and pH electrode and carefully neutralized with 82 g of sodium hydroxide solution (50%). After neutralization, the sodium chloroacetate mixture was admixed with 52.4 g of magnesium chloride hexahydrate and heated to 70°–80° C. After addition of 320 g of the aminamide from Example 1, the reaction mixture was stirred at 80°–90° C., the pH being kept between 8 and 8.5. For this purpose, a further total of 10.3 g of sodium hydroxide (as 50% strength solution) were required. After a reaction time of about 8 hours, the alkylation was complete. a betaine mixture had formed and was allowed to cool to 50° C. and the pH was adjusted to 5.8 using 5.4 g of citric acid.

The final product was a clear liquid having a viscosity of 112 mPas at 20° C., a dry residue of 45.1% and a chloride content of 5.1%.

Example 8

97.3 g of monochloroacetic acid solution were carefully neutralized with 82 g of sodium hydroxide solution (50%) while cooling in a 1 liter flask fitted with stirrer, internal thermometer and pH electrode. After neutralization, the sodium chloroacetate mixture was admixed with 26 g of magnesium chloride hexahydrate and heated to 70°–80° C. After addition of 320 g of the aminamide from Example 1, the reaction mixture was stirred at 80°–90° C., the pH being kept between 8 and 8.5. For this purpose, a further total of 5.3 g of sodium hydroxide (as 50% strength solution) were required. After a reaction time of about 8 hours, the alkylation was complete. A betaine mixture had formed and was allowed to cool to 50° C. and the pH was adjusted to 5.9 using 3.5 g of citric acid.

The final product was a clear liquid having a viscosity of 107 mPas at 20° C., a dry residue of 44.4% and a chloride content of 4.3%.

Example 9

97.3 g of monochloroacetic acid were diluted with 535 g of water while cooling in a 1 liter flask fitted with stirrer, internal thermometer and pH electrode and carefully neutralized with 32 g of magnesium hydroxide. After addition of 24.3 g of trimethylglycine and 320 g of the amminamide from Example 1, the reaction mixture was stirred at 80°–90° C., the pH being kept between 8 and 8.5. For this purpose, a further total of 7.3 g of magnesium hydroxide were required. After a reaction time of about 8 hours, the alkylation was complete. A betaine mixture had formed and was allowed to cool to 50° C. and the pH was adjusted to 5.7 using 18 g of citric acid monohydrate.

The final product was a clear liquid having a viscosity of 132 mPas at 20° C., a dry residue of 45.4% and a chloride content of 3.5%.

What is claimed is:

1. A process for preparing a highly concentrated, free-flowing and pumpable, aqueous solutions of one or more betaines, comprising quaternizing one or more compounds containing tertiary amine nitrogen of the formula (I)

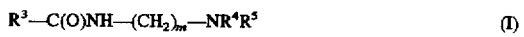

wherein $R^3$ is alkyl or alkylene containing 6 to 20 carbon atoms and 0–3 carbon-carbon double bonds, and is optionally substituted with 1–6 hydroxyl groups, m is 1–3, and $R^4$ and $R^5$ are independently alkyl containing 1 to 4 carbon atoms, with omega-halocarboxylic acid in the presence of 0.5–5% by weight, based on the total mixture, of at least one ionic or internal salt selected from the group consisting of

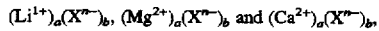

and one or more compounds of the general formula (IV)

where R $R^1$, $R^2$ are independently identical or different, straight or branched alkyl radicals having 1–10 carbon atoms, optionally substituted with 1 to 6 hydroxyl groups and n is 1–3,
wherein $X^{n-}$ is the radical of an organic or inorganic acid, n is 1–3, a and b are integers, and the values of a, b and n are selected such that the net charge of the compounds is neutral, and in the presence of the Na, K or $NH_4$ salt of the omega-halocarboxylic acid, wherein said one or more ionic or internal salts is added before or during said quaternization.

2. A betaine solution prepared according to claim 1, characterized in that it contains at least 35% by weight of one or more compounds of the general formula (III)

wherein y is 1–3 and $R^3$, m, $R^4$ and $R^5$ are as defined with respect to formula (I); and 0.5–5% by weight of at least one lithium, magnesium or calcium salt with an anion of the formula $X^{n-}$.

3. A process for preparing a highly concentrated, free-flowing and pumpable, aqueous solution of one or more betaines, comprising quaternizing one or more compounds containing tertiary amine nitrogen of the formula (I)

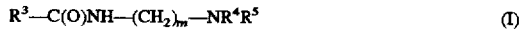

wherein $R^3$ is alkyl or alkylene containing 6 to 20 carbon atoms and 0–3 carbon-carbon double bonds, and is optionally substituted with 1–6 hydroxyl groups, m is 1–3, and $R^4$ and $R^5$ are independently alkyl containing 1 to 4 carbon atoms, with omega-halocarboxylic acid in the presence of 0.5–5% by weight, based on the total mixture, of at least one salt selected from the group consisting of

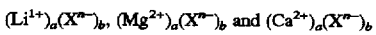

wherein $X^{n-}$ is the radical of an organic or inorganic acid, n is 1–3, a and b are integers, and the values of a, b and n are selected such that the net charge of the compounds is neutral, and in the presence of the Na, K or $NH_4$ salt of the omega-halocarboxylic acid, wherein said salts are added before or during said quaternization.

4. A process according to claim 3, characterized in that $X^{n-}$ is the radical of a monobasic organic or inorganic acid.

5. A process according to claim 3, characterized in that $X^{n-}$ is the anion $Cl^-$.

6. A betaine solution prepared according to claim 3, characterized in that it contains at least 35% by weight of one or more compounds of the general formula (III)

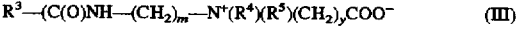

wherein y is 1–3 and $R^3$, m, $R^4$ and $R^5$ are as defined with respect to formula (I); and 0.5–5% by weight of at least one lithium, magnesium or calcium salt with an anion of the formula $X^{n-}$.

7. A betaine solution prepared according to claim 4, characterized in that it contains at least 35% by weight of one or more compounds of the general formula (III)

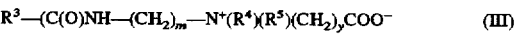

wherein y is 1–3 and $R^3$, m, $R^4$ and $R^5$ are as defined with respect to formula (I); and 0.5–5% by weight of at least one lithium, magnesium or calcium salt with an anion of the formula $Xn^{n-}$.

8. A betaine solution prepared according to claim 5, characterized in that it contains at least 35% by weight of one or more compounds of the general formula (III)

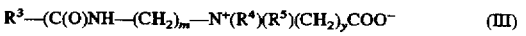

wherein y is 1–3 and $R^3$, m, $R^4$ and $R^5$ are as defined with respect to formula (I); and 0.5–5% by weight of at least one lithium, magnesium or calcium salt with an anion of the formula $X^{n-}$.

9. A process for preparing a highly concentrated, free-flowing and pumpable, aqueous solution of one or more betaines, comprising quaternizing one or more compounds containing tertiary amine nitrogen with omega-halocarboxylic acid in the presence of a) 30–100 equivalent-%, based on the amount of omega-halocarboxylic acid reacted, of one or more of LiOH, $Mg(OH)_2$ and $Ca(OH)_2$ and b) 0–70 equivalent-%, based on the amount of omega-halocarboxylic acid reacted, of one or more of NaOH, KOH, and $NH_4OH$ wherein said one or more hydroxides a) and, if present b) is added before or during said quaternization.

10. A process according to claim 9, characterized in that the omega-halocarboxylic acid used is chloroacetic acid.

11. A process according to claim 9, characterized in that the component a) is 30–100 equivalent-%, based on the amount of omega-halocarboxylic acid reacted, of LiOH.

12. A betaine solution prepared according to claim 9, wherein the solution contains 30–100 equivalent-% of salts of lithium, magnesium, or calcium or mixtures of one or more thereof.

13. A betaine solution prepared according to claim 10 wherein the solution contains 30–100 equivalent-% of salts of lithium, magnesium, or calcium or mixtures of one or more thereof.

14. A betaine solution prepared according to claim 11 wherein the solution contains 3–100 equivalent-% of salts of lithium, magnesium, or calcium or mixtures of one or more thereof.

15. A betaine solution prepared according to claim 9 containing at least 35% by weight of one or more compounds of the general formula $$R^3-C(O)NH-(CH_2)_{1-3}-N^+(R^4)(R^5)-(CH_2)_{1-3}C(O)O^- \quad (III)$$

wherein $R^3$ is alkyl or alkylene containing 6 to 20 carbon atoms and 0–3 carbon-carbon double bonds, and is optionally substituted with 1–6 hydroxyl groups, and $R^4$ and $R^5$ are independently alkyl containing 1 to 4 carbon atoms;

4–8% by weight if at least one lithium, magnesium, or calcium salt; and water to 100%.

16. A betaine solution prepared according to claim 10 containing at least 35% by weight of one or more compounds of the general formula $$R^3-C(O)NH-(CH_2)_{1-3}-N^+(R^4)(R^5)-(CH_2)_{1-3}C(O)O^- \quad (III)$$

wherein $R^3$ is alkyl or alkylene containing 6 to 20 carbon atoms and 0–3 carbon-carbon double bonds, and is optionally substituted with 1–6 hydroxyl groups, and $R^4$ and $R^5$ are independently alkyl containing 1 to 4 carbon atoms;

4–8% by weight if at least one lithium, magnesium, or calcium salt; and water to 100%.

17. A betaine solution prepared according to claim 11 containing at least 35% by weight of one or more compounds of the general formula $$R^3-C(O)NH-(CH_2)_{1-3}-N^+(R^4)(R^5)-(CH_2)_{1-3}C(O)O^- \quad (III)$$

wherein $R^3$ is alkyl or alkylene containing 6 to 20 carbon atoms and 0–3 carbon-carbon double bonds, and is optionally substituted with 1–6 hydroxyl groups, and $R^4$ and $R^5$ are independently alkyl containing 1 to 4 carbon atoms;

4–8% by weight if at least one lithium, magnesium, or calcium salt; and water to 100%.

* * * * *